United States Patent
Nakamura et al.

(12)

(10) Patent No.: US 6,214,802 B1
(45) Date of Patent: Apr. 10, 2001

(54) PERITONEAL DIALYSIS FLUID

(75) Inventors: Yukio Nakamura; Shiho Yamaguchi; Yasuhiro Tsutsui; Takeo Kikuchi, all of Osaka (JP)

(73) Assignee: Nissho Corporation, Osaka (JP)

( * ) Notice: Subject to any disclaimer, the term of this patent is extended or adjusted under 35 U.S.C. 154(b) by 0 days.

(21) Appl. No.: 09/316,186

(22) Filed: May 21, 1999

(30) Foreign Application Priority Data

May 21, 1998 (JP) .................................................. 10-139295

(51) Int. Cl.⁷ .......................... A61K 31/70; A61K 38/00; A61K 31/715
(52) U.S. Cl. .................................. 514/23; 514/2; 514/53; 514/54
(58) Field of Search ................................... 514/2, 23, 53, 514/54

(56) References Cited

U.S. PATENT DOCUMENTS

| 4,976,683 | 12/1990 | Gauthier et al. | 604/29 |
|---|---|---|---|
| 5,011,826 | 4/1991 | Steudle et al. | 514/23 |
| 5,597,805 | 1/1997 | Breborowicz et al. | 514/19 |
| 5,780,438 | 7/1998 | Gilchrist et al. | 514/21 |
| 5,869,444 | 2/1999 | Klein | 514/2 |

OTHER PUBLICATIONS

Carlsson et al., "In vivo inhibition of transcellular . . . ", Am J Physiol, 271 (6 Pt 2):H2254–62 1996, Dec at (http://www/infotrieve.com/freemedline/cg . . . ).

Park et al., "Albumin–based Solutions for Peritoneal Dialysis: Investigations . . . ", Artificial Organs, 19(4):307–314, 1995.

The Sigma Catalog, Albumin Standards (p. 70), 1993.*

Comstock, T. "Renal Dialysis—Chapter 31", Applied Therapeutics—The clinical use of drugs (sixth ed.), edited by Young and Koda–Kimble, pp. 31–1 to 31–15, 1995.*

Yeun et al. "Factors influencing serum albumin in dialysis patients", Amer. J. of Kidney Dis., vol. 32: S118–S125, 1998.*

Spiegel et al. "Serum albumin: a predictor of long–term outcome in peritoneal dialysis patients", Am. J. Kidney Dis., vol. 23: 283–285, 1994.*

Flanigan et al. "1996 peritoneal dialysis—core indicators report", Am. J. Kidney Dis., vol. 32: E2–E3, 1998.*

Khanna, R. "When Will New Peritoneal Dialysis Solutions Being Used Abroad Be Available in the USA?", Peritoneal Dialysis Today, vol. 5(1), Feb. 1999.*

Tzamaloukas, A. "Hypertonic Peritoneal Dialysis Solutions Can Enhance Peritoneal Clearance", Peritoneal Dialysis Today, vol. 5(1), Feb. 1999.*

* cited by examiner

Primary Examiner—Howard C. Lee
(74) Attorney, Agent, or Firm—Kubovcik & Kubovcik

(57) ABSTRACT

A peritoneal dialysis fluid characterized by the addition of 0.1 to 30 g/L of albumin. The peritoneal dialysis fluid reduces the occurrence of peritonitis during peritoneal dialysis.

11 Claims, No Drawings

PERITONEAL DIALYSIS FLUID

FIELD OF THE INVENTION

The present invention relates to a peritoneal dialysis fluid. More particularly, it relates to a peritoneal dialysis fluid that can suppress occurrence of peritonitis resulting from peritoneal dialysis.

BACKGROUND OF THE INVENTION

In the event of renal failure, it becomes difficult to excrete the final nitrogen metabolites and the like from the human body and they accumulate within the body to cause dysfunction to various organs. For this reason, a medical treatment by artificial dialysis is conducted in order to excrete the accumulated metabolites outside the body. Artificial dialysis is roughly classified into haemodialysis and peritoneal dialysis.

The aim of haemodialysis is to excrete excess water, unwanted solutes, small molecular weight substances like urea and creatinine and other uremic substances in order to correct their levels. Therefore, the usual procedure is that blood is withdrawn from a patient and is passed through a dialyser outside the body using a dialysis fluid. Recently a dialysis fluid mainly containing sodium bicarbonate which is an alkaline agent is used. This haemodialysis treatment is capable of being combined with blood absorption or plasma separation procedures, which is frequently adopted. This treatment has an advantage that it can be applied to patients for a long term period, whereas it has such defects that use of the dialysis apparatus requires a great deal of cost, that patients must have a surgical procedure to provide blood access for blood extracorporeal circulation, that its application is limited to patients who have cardiopulmonary functions strong enough to endure extracorporeal circulation, and so on.

On the other hand, peritoneal dialysis is a method for exchanging solutes and water in capillary vessels of a patient's peritoneal with hypertonic solution which is injected within the peritoneal cavity. The principle of this method is diffusion of solutes which are transferred according to the concentration gradient and water migration due to the osmotic differences. Azotemia, and imbalance of water and electrolytes are corrected by this principle. This method has many advantages such that no special apparatus is commonly required and it gives less influence on the hemodynamics because extracorporeal circulation of the patient's blood is not necessary, and further the peritoneal dialysis is similar to the physiological function of the kidney.

Peritoneal dialyses are usually classified as Continuous Ambulatory Peritoneal Dialysis(CAPD), Intermittent Peritoneal Dialysis (IPD) or Continuous Cyclic Peritoneal Dialysis(CCPD).

The dialysis fluid used for peritoneal dialysis is an aqueous solution which comprises an osmotic agent such as glucose and the like, electrolytes such as sodium, potassium, calcium, magnesium, and organic acid salts such as sodium lactate. These peritoneal dialysis fluids are determined according to the components so as to control the levels of electrolytes or acid-base equilibrium, remove the waste materials and efficiently carry out ultrafiltration.

However, peritoneal dialysis fluids have heretofore been maintained at acidic pH, 4.5 to 5.5, for their compositional stability and their osmotic pressure has been rendered hypertonic for dialyzing effects, that is the osmotic pressure ratio to physiological saline is about 1.1 to 1.6. Clinically, dialysis fluids which are unsuitable for the human body are intraperitoneally injected in large amounts, for instance about 10 L/human/day and pooled in the peritoneal cavity for several hours, for instance 2 to 24 hours. Accordingly, there is a defect that patients who are subjected to dialysis tend to suffer peritonitis, etc., accompanied by clinical symptoms such as stomach ache, and finally peritoneal sclerosis, etc. (Wakabayashi, Y. and Kawaguchi, Y.; "Peritoneal Dialysis and Sclerosing Encapsulating Peritonitis", Igaku No Ayumi (Progress in Medical Science), 183, 363–367, 1997). Occurrence of peritoneal sclerosis decreases the degree of effectiveness of dialysis, which makes it difficult for patients suffering kidney diseases to use peritoneal dialysis for a long term period. Further there are defects that plasma proteins are lost and the period of dialysis is very long and so on.

Under these circumstances, the present invention has been made and, therefore, an object of the present invention is to provide a peritoneal dialysis fluid that can suppress the occurrence of peritonitis.

SUMMARY OF THE INVENTION

As a result of intensive research by the present inventors in view of solving the above-described problems, it has now been found that an addition of a suitable amount of albumin to a peritoneal dialysis fluid considerably suppresses the occurrence of peritonitis, thus completing the present invention. That is, the present invention relates to a peritoneal dialysis fluid containing 0.1 to 30 g/L of albumin.

Conventionally albumin is known to be used in dialysis fluid as an osmotic agent (for instance, Japanese Patent Publication No.63-3871, Japanese Patent Publication No.1-313061, Artificial Organ, 1995, 19(4), 307–314). However, because the albumin shows a less osmotic effect than that of lower molecular weight substances as a dialysis osmotic agent, extremely high amounts of albumin are necessary to excrete high amounts of water, that is, ultrafiltration. For instance, the amount of the albumin as an osmotic agent is about 75 g per one liter of dialysis fluid which is relatively high. The high amounts of albumin cause an uptake into the living body and the increased amount of albumin in the body causes a disorder of serum osmolarity. The present invention is characterized by the use of smaller amounts of albumin than when used as conventional osmotic agents.

The dialysis fluid in the present invention comprises electrolytes, an osmotic agent not including albumin, physiologically acceptable pH solution and 0.1 to 30 g/L of human serum albumin.

The osmotic pressure of the peritoneal dialysis fluid in the present invention, that is, the ratio of the osmotic pressure of the dialysis fluid to that of physiological saline, is 1.0 to 3.0, preferably 1.1 to 1.6. The physiologically acceptable pH is 4.0 to 8.0, preferably 4.5 to 7.5, most preferably 5.0 to 7.4.

Albumin which can be used in the present invention is that derived from mammals such as humans, bovines and the like, or manufactured by chemical synthesis or genetic techniques. Preferably, human serum albumin including that manufactured by the genetic techniques is used.

Here, the amount of albumin is 0.1 to 30 g/L, preferably 0.1 to 5 g/L. An amount of less than 0.1 g/L of albumin exhibits a low peritonitis suppressing effect while use of an amount of more than 30 g/L of albumin results in increased water migration from the body to the peritoneal dialysis fluid. Substantially more than 30 g/L of albumin causes an increased level of serum albumin so as to change serum osmolarity, such as shown in rats in Example 5 described below.

The peritoneal dialysis fluid may contain sodium N-acetyltryptophan, sodium caprylate, etc., as an albumin stabilizer. The amount of the albumin stabilizer is 5 to 50 mg per 1 gram of albumin.

The osmotic agent in the present invention is one or two or more compounds selected from the group consisting of glycerol, monosaccharides, disaccharides, polysaccharides, sugar alcohols, gelatin and amino acids. The monosaccharides can include glucose, fructose, galactose, etc., and disaccharides can include sucrose, maltose, trehalose, etc. The polysaccharides can include dextrin, starch, polyglucose, hydroxyethylstarch and other carbohydrates and the sugar alcohols can include xylytol, mannitol, sorbitol, etc. Additionally, other useful high molecular weight substances include gelatin, hyaluronic acid, etc. The amount of the osmotic agent is generally about 5 to 200 g/L. Specifically, about 10 to 70 g/L of monosaccharide, about 20 to 140 g/L of disaccharide or about 30 to 100 g/L of polysaccharide can be used. The amino acids can be a mixture of essential amino acids and nonessential amino acids of which the amount is in the range of about 5 to 30 g/L. Glucose is preferably used as an effective osmotic agent in the dialysis fluid in the present invention.

In addition to an osmotic agent it is also usual to include in the dialysis fluid effective electrolytes in concentrations which are substantially isotonic. The electrolytes may contain positive ions such as alkali metal ions, alkaline earth metal ions, etc., and negative ions such as chloride ion, etc. Alkali metals include sodium, potassium, etc., and alkaline earth metals include calcium, magnesium, etc. The amount of positive ions can be generally 110 to 140 mEq/L of sodium ion, 0 to 0.05 mEq/L of potassium ion, 0 to 3 mEq/L of magnesium ion and 0 to 6 mEq/L of calcium ion. Preferably the amount of chloride ion is 80 to 144 mEq/L.

The dialysis fluid of the present invention is preferably regulated by pH adjusting agents such as inorganic acids, organic acids, alkali substances, etc. in a pharmaceutically stable range. Inorganic acids include hydrochloric acid, etc., organic acids include lactic acid, malic acid, acetic acid, succinic acid, maleic acid, pyruvicacid, citric acid, etc., andalkali substances include sodium hydrate, sodium bicarbonate, etc.

As an example of a suitable dialysis fluid, there can be mentioned compositions that contain a portion of or all the following components.

| | |
|---|---|
| Glucose | 5 to 45 g/L |
| Electrolyte | |
| Sodium ion | 120 to 140 mEq/L |
| Calcium ion | 2.0 to 5.0 mEq/L |
| Magnesium ion | 0.3 to 3.0 mEq/L |
| Chloride ion | 80 to 120 mEq/L |
| Lactate ion | 10 to 50 mEq/L |
| Bicarbonate ion | 0 to 25 mEq/L |
| Albumin | 0.1 to 30 g/L |

The dialysis fluid in the present invention can also contain a small amount of chitosan, sodium alginate, etc., as an adhesion preventing agent for the peritoneum, if desired. Further, as the osmotic agent, there can be used monosaccharides (fructose, etc.), disaccharides (sucrose, etc.) and carbohydrates (dextran, starch, etc.) in place of said glucose.

As for the pH adjusting agent, organic acid salts such as acetates and citrates can be used in place of lactates or bicarbonates. Also, various amino acids can be used as a pH adjusting agent or osmotic pressure regulating agent. Since peritoneal dialysis methods involve leakage of nutrients from the blood to the dialysis fluid, in case of no nutrients being contained in the dialysis fluid, there can be used peritoneal dialysis fluids containing the nutrients that are to be leaked.

In Continuous Ambulatory Peritoneal Dialysis(CAPD) a catheter is permanently indwelled in the abdomen wall of the patient and about 1.5 to 2 L of the dialysis fluid is introduced via the catheter into the peritoneal cavity. The peritoneal cavity is flooded with this fluid, left for an appropriate lapse of time and then drained. Removal of solutes and water takes place across the peritoneum which acts as a semi-permeable membrane. The peritoneal dialysis fluid of the present invention is applicable for not only said Continuous Ambulatory Peritoneal Dialysis (CAPD) but also Intermittent Peritoneal Dialysis (IPD) or Continuous Cyclic Peritoneal Dialysis (CCPD) as Automated Peritoneal Dialysis (APD)

In order to illustrate the present invention, dialysis fluids according to the present invention will be described in the following examples.

EXAMPLE1

Test for Confirming the Effect of Preventing Occurrence of Peritonitis

Healthy male SD rats (aged 5 to 6 weeks) were starved for 24 hours. Each test group was intraperitoneally administered with 100 mL/kg of a dialysis fluid having the composition shown in Table 1 to which had been added 0.1, 0.3, 1, 5, or 10 g/L of human serum albumin (HSA). After 40 minutes from the administration, 2 mg/mL FITC-albumin (bovine serum albumin labeled with fluorescein isothiocyanate) as a dye-labeled protein was administered in a proportion of 0.9 mg/kg in a rat tail vein. After 20 minutes, the rats were exsanguinated to death under anesthesia with ether and abdominal ascites (recovered dialysis fluid) was collected. The ascites was measured for the concentration of the fluorescein dye-labeled protein therein by a fluorescence spectrophotometer (excitation wavelength: 494 nm, emission wavelength: 523 nm) and the concentration of leaked fluorescent protein was calculated. The results are shown in Table 2.

TABLE 1

| | Physiological saline | Peritoneal dialysis fluid |
|---|---|---|
| Glucose | — | 13.6 g |
| Sodium chloride | 9 g | 5.38 g |
| Sodium lactate | — | 4.48 g |
| Calcium chloride | — | 0.257 g |
| Magnesium chloride | — | 0.00508 g |
| Distilled water for injection | 1,000 mL | 1,000 mL |

TABLE 2

| Test Group: Amount of HSA added (g/L) | Number of rats | Concentration of leaked fluorescent protein (pg/mL) | Suppression (%) |
|---|---|---|---|
| Physiological saline | 8 | 0.651 ± 0.053** | |
| Peritoneal dialysis Fluid | 8 | 1.886 ± 0.208## | |

TABLE 2-continued

| Test Group: Amount of HSA added (g/L) | Number of rats | Concentration of leaked fluorescent protein (pg/mL) | Suppression (%) |
|---|---|---|---|
| +0.1 | 6 | 1.195 ± 0.088**# | 56.0 |
| +0.3 | 6 | 1.025 ± 0.086**# | 69.7 |
| +1 | 7 | 0.958 ± 0.166** | 75.1 |
| +5 | 9 | 0.620 ± 0.089** | 102.5 |
| +10 | 9 | 0.459 ± 0.100** | 115.5 |

Note: Numerical values are the mean ± SEM and Dunnett multiple comparison test was adopted.
**Significant difference from the group administered with a peritoneal dialysis fluid alone at $P < 0.01$.
, ##Significant difference from the group administered with physiological saline at $P < 0.05$ and $P < 0.01$, respectively.

Suppression (%)=(the concentration of leaked fluorescent protein of the group administered with a peritoneal dialysis fluid alone—the concentration of leaked fluorescent protein of the group administered with a peritoneal dialysis fluid to which albumin is added/the concentration of leaked fluorescent protein of the group administered with a peritoneal dialysis fluid alone—the concentration of leaked fluorescent protein of the group administered with physiological saline)×100.

From Table 2, it is observed that the group administered with a peritoneal dialysis fluid without HSA showed a significant increase in the concentration of fluorescein dye-labeled protein in the ascites as compared with the group administered with physiological saline, i.e., control group. From the results, which show a decrease of the amount of leaked albumin according to the addition of HSA, which is an index of peritonitis, it is considered that occurrence of peritonitis can be suppressed.

EXAMPLE 2

Test for Conforming the Effect of Preventing Occurrence of Peritonitis

Healthy male SD rats (aged 5 to 6 weeks) were starved for 24 hours. Each test administration group was intraperitoneally administered with 100 mL/kg of a dialysis fluid having the composition shown in Table 1 to which had been added 0.1, 1 or 10 g/L of recombinant human serum albumin (r-HSA), and the same tests as in Example 1 were carried out. Table 3 shows the results.

TABLE 3

| Test Group: Amount of r-HSA added (g/L) | Number of rats | Concentration of leaked fluorescent Protein (µg/mL) | Suppression (%) |
|---|---|---|---|
| Physiological saline | 6 | 0.694 ± 0.105** | |
| Peritoneal dialysis Fluid | 5 | 1.810 ± 0.210## | |
| +0.1 g/L of r-HSA | 6 | 1.120 ± 0.108** | 61.8 |
| +1 g/L of r-HSA | 5 | 0.975 ± 0.135** | 74.8 |
| +10 g/L of r-HSA | 6 | 0.512 ± 0.089** | 116.3 |

Note: Numerical values are the mean ± SEM and Dunnett multiple comparison test was adopted.
**Significant difference from the group administered with a peritoneal dialysis fluid alone at $P < 0.01$.
Significant difference from the group administered with physiological saline at $P < 0.01$.

Suppression (%)=(the concentration of leaked fluorescent protein of the group administered with a peritoneal dialysis fluid alone—the concentration of leaked fluorescent protein of the group administered with a peritoneal dialysis fluid to which albumin is added/the concentration of leaked fluorescent protein of the group administered with a peritoneal dialysis fluid alone—the concentration of leaked fluorescent protein of the group administered with physiological saline)×100.

From Table 3, it is observed that the group administered with a peritoneal dialysis fluid containing no r-HSA showed a significant increase in the concentration of dye-labeled protein in the ascites as compared with the group administered with physiological saline, i.e., control group. Also, it is observed that addition of r-HSA caused a concentration-dependent decrease in concentration of fluorescein dye-labeled protein in the ascites. From the results, it is suggested that addition of r-HSA can suppress occurrence of peritonitis.

EXAMPLE 3

Test for Confirming the Effect of Preventing Occurrence of Peritonitis

Healthy male SD rats (aged 5 to 6 weeks) were starved for 24 hours. Each test administration group was intraperitoneally administered with 100 mL/kg of a dialysis fluid having the composition shown in Table 1 to which had been added 0.1, 0.3, 1, 3 or 10 g/L of bovine serum albumin (BSA), and the same tests as in Example 1 were carried out. Results are shown in Table 4.

TABLE 4

| Test Group: Amount of BSA added (g/L) | Number of rats | Concentration of leaked fluorescent protein (µg/mL) | Suppression (%) |
|---|---|---|---|
| Physiological saline | 8 | 0.651 ± 0.053** | |
| Peritoneal dialysis fluid | 8 | 1.886 ± 0.208## | |
| +0.1 g/L of BSA | 6 | 1.395 ± 0.075### | 39.8 |
| +0.3 g/L of BSA | 6 | 1.220 ± 0.155**# | 53.9 |
| +1 g/L of BSA | 7 | 0.983 ± 0.064** | 73.1 |
| +3 g/L of BSA | 9 | 0.920 ± 0.089** | 78.2 |
| +10 g/L of BSA | 9 | 0.821 ± 0.118** | 86.2 |

Note: Numerical values are the mean ± SEM and Dunnett multiple comparison test was adopted.
*, **Significant difference from the group administered with a peritoneal dialysis fluid alone at $P < 0.05$ and $P < 0.01$, respectively.
,##: Significant difference from the group administered with physiological saline at $P < 0.05$ and $P < 0.01$, respectively.

Suppression (%)=(the concentration of leaked fluorescent protein of the group administered with a peritoneal dialysis fluid alone—the concentration of leaked fluorescent protein of the group administered with a peritoneal dialysis fluid to which albumin is added/the concentration of leaked fluorescent protein of the group administered with a peritoneal dialysis fluid alone—the concentration of leaked fluorescent protein of the group administered with physiological saline)×100.

From Table 4, it is observed that the group administered with a peritoneal dialysis fluid containing no BSA showed a significant increase in the concentration of fluorescein dye-labeled protein in the ascites as compared with the group administered with physiological saline, i.e., control group. Also, it is observed that addition of BSA caused a concentration-dependent decrease in concentration of fluorescein dye-labeled protein in the ascites.

From the results, it is suggested that addition of BSA can suppress occurrence of peritonitis.

EXAMPLE 4

Healthy male SD rats (aged 6 to 7 weeks) were starved for 24 hours. Each test administration group was intraperitoneally administered with 100 mL/kg of a dialysis fluid having the composition shown in Table 1, or a dialysis fluid having the composition shown in Table 1 and containing either 5 μg/mL of lipopolysaccharide (LPS) or 5 μg/mL of LPS and 3 mg/mL of rat serum albumin (RSA).

After 18 hours from the administration, the rats were exsanguinated to death under anesthesia with ether and ascites was collected and measured for the number of leukocytes therein. The results are shown in Table 5.

TABLE 5

| Test Group | LPS (5 μg/mL) | RSA (3 mg/mL) | Number of leukocytes in ascites (× $10^8$, leukocytes/animal) |
|---|---|---|---|
| 1 | − | − | 2.9 ± 0.3 |
| 2 | + | − | 4.15 ± 0.79 |
| 3 | + | + | 2.94 ± 0.38 |

Note: Numerical values are the mean ± SEM. Each test group consists of 5–6 rats.

From Table 5, it is observed that the group administered with a peritoneal dialysis fluid containing LPS showed a significant increase in the number of leukocytes in the ascites as compared with the group administered with the dialysis fluid alone, while the group administered with a peritoneal dialysis fluid containing both LPS and RSA showed a similar decrease in the number of leukocytes in the ascites as that administered with dialysis fluid alone. From the results, it is suggested that RSA can suppress the occurrence of peritonitis caused by LPS which resembles bacteria infected peritonitis.

EXAMPLE 5

Healthy male SD rats (aged 5 to 6 weeks) were starved for 24 hours. Each test group was intraperitoneally administered with 100 mL/kg of a dialysis fluid having the composition shown in Table 1 to which had been added 0.1, 1.0, 5.0, 10.0, 30.0, 50.0 or 100.0 g/L of bovine serum albumin (BSA). After 4 hours from the administration, the rats were exsanguinated to death under anesthesia with ether and the blood was collected. The serum was obtained from the blood by centrifugation, and the level of albumin and urea nitrogen were determined. The measurement of albumin used a commercially available clinical measurement kit (Albumin Test Wako, manufactured by Wako Pure Chemical Industry Co., Ltd.). The results are shown in Table 6. Each value for a group is compared with that of non-treated rats.

TABLE 6

| Test Group: Amount of BSA added (g/L) | Number of rats | Concentration of albumin in blood (mg/dL) |
|---|---|---|
| non treated rat | 4 | 3.5 ± 0.0 |
| Peritoneal dialysis fluid | 4 | 3.5 ± 0.1 |
| +0.1 g/L of BSA | 4 | 3.5 ± 0.1 |
| +1.0 g/L of BSA | 4 | 3.5 ± 0.1 |
| +5.0 g/L of BSA | 4 | 3.7 ± 0.1 |
| +10.0 g/L of BSA | 4 | 3.7 ± 0.1 |
| +50.0 g/L of BSA | 4 | 4.1 ± 0.0**## |
| +100.0 g/L of BSA | 4 | 4.3 ± 0.1**## |

Note: Numerical values are the mean ± SEM and Dunnett multiple comparison test was adopted.
**Significant difference from the group administered with a peritoneal dialysis fluid alone at P < 0.01
: Significant difference from normal animal group at P < 0.01.

From Table 6, it is observed that the group administered with peritoneal dialysis fluid alone or with the fluid containing 0.1 to 10.0 g/L of BSA showed no significant difference in the level of albumin in the blood as compared with the group of non treated rats. On the other hand the group administered with the fluid containing 50 to 100 g/L of BSA showed a significantly higher level of albumin in the blood as compared with non treated rats. Therefore, it is supposed that patients treated with a high amount of albumin-containing fluid will show a remarkable increase of serum albumin, which causes an increase of colloidal osmolarity. Further the occurrence of azotemia will be possibly caused from the high amount administration of albumin in the peritoneum, therefore it is not preferable to add more than 30 g/L of albumin into the peritoneal dialysis fluid.

EXAMPLE 6

Test for Confirming the Effect of Dialysis

Healthy male SD rats (aged 5 weeks) were anesthetized and their back skin was cut to expose the kidneys. After the renal artery and vein were simultaneously ligated, a bilateral nephrectomy was done. The cut portion was sutured and the animals were starved for 20 hours, each administration group was intraperitoneally administered 100 mL/kg of a dialysis fluid having the composition shown in Table 1 to which had been added 0.1, 1, 5, 10 or 30 g/L of recombinant human serum albumin (r-HSA). After 4 hours, the ascites (recovered dialysis fluid) was collected and the amount of the fluid and urea nitrogen level were determined. The results are shown in Table 7. For the measurement of urea nitrogen there was used a commercially available clinical measurement kit (Urea Nitrogen B Test Wako, manufactured by Wako Pure Chemical Industry Co., Ltd.).

TABLE 7

| Test group: Amount of HSA added (g/L) | Number of rats | Amount of recovered dialysis fluid (mL/kg) | Urea nitrogen in dialysis fluid (mg/dl) |
|---|---|---|---|
| Physiological saline | 6 | 36.0 ± 3.1 | 30.8 ± 3.8 |
| Peritoneal dialysis fluid | 5 | 55.1 ± 3.4## | 56.8 ± 5.3# |
| +0.1 g/L of HSA | 4 | 56.4 ± 7.4# | 66.1 ± 13.1## |
| +1 g/L of HSA | 4 | 60.2 ± 4.7## | 68.3 ± 9.1## |
| +5 g/L of HSA | 4 | 56.8 ± 3.7## | 65.8 ± 5.6## |
| +10 g/L of HSA | 6 | 49.9 ± 5.6 | 54.2 ± 4.6## |
| +30 g/L of HSA | 6 | 52.6 ± 7.7 | 60.0 ± 0.9## |

Note: Numerical values are the mean ± SEM and Student's-t test was adopted.
, ##Significant difference from the group administered with physiological saline at P < 0.05 and P < 00.01, respectively.

From Table 7, it is observed that the groups administered with a peritoneal dialysis fluid showed a significant increase in urea nitrogen content in the dialysis fluid as compared with the group administered with physiological saline and it is confirmed that the peritoneal dialysis fluid has a dialyzing effect. With the addition of 0.1 to 5 g/L of HSA, no difference was observed in the amount of recovered dialysis fluid while with the addition of 10 g/l or 30 g/l of HSA, a decrease in the amount of recovered dialysis fluid was observed. From these results, it is considered that the addition of 0.1 to 5 g/L of r-HSA gives no influence on the effect of dialysis.

As described above, it is apparent that use of the peritoneal dialysis fluid of the present invention provides a significant suppression of occurrence of peritonitis caused by peritoneal dialysis fluid.

What is claimed is:

1. A peritoneal dialysis fluid containing electrolytes, an osmotic agent other than albumin, physiologically acceptable pH solution and 0.1 to 30 g/L of albumin.

2. The peritoneal dialysis fluid as claimed in claim 1, wherein said electrolytes comprise sodium ion and chloride ion.

3. The peritoneal dialysis fluid as claimed in claim 1, wherein said electrolytes comprise 110 to 140 mEq/L of sodium ion, 0 to 0.05 mEq/L of potassium ion, 0 to 2 mEq/L of magnesium ion, 0 to 6 mEq/L of calcium ion, and 80 to 144 mEq/L of chloride ion.

4. The peritoneal dialysis fluid as claimed in claim 1, wherein said osmotic agent is one or two or more compounds selected from the group consisting of glycerol, monosaccharide, disaccharide, polysaccharide, sugar alcohol, gelatin, hyaluronic acid and amino acid.

5. The peritoneal dialysis fluid as claimed in claim 1, wherein said physiologically acceptable pH solution has pH 4.5 to 7.5.

6. The peritoneal dialysis fluid as claimed in claim 1, having an osmotic pressure ratio of dialysis fluid to physiological saline of 1.1 to 3.0.

7. The peritoneal dialysis fluid as claimed in claim 1, wherein said physiologically acceptable pH solution contains an agent for adjusting pH in the peritoneal solution.

8. The peritoneal dialysis fluid as claimed in claim 7, wherein the pH adjusting agent is one or more compounds selected from the group consisting of hydrochloric acid, lactic acid, acetic acid, citric acid, malic acid, maleic acid, pyruvic acid, succinic acid, sodium hydroxide, and sodium bicarbonate.

9. A peritoneal dialysis fluid comprising the following composition which has a physiologically acceptable pH of 4.5 to 7.5,

| (1) osmotic agent selected from the group consisting of glycerol, monosaccharide, disaccharide, polysaccharide, sugar alcohol, gelatin and amino acids | 5 to 200 g/L |
|---|---|
| (2) electrolyte | |
| sodium ion | 110 to 140 mEq/L |
| potassium ion | 0 to 0.05 mEq/L |
| magnesium ion | 0 to 3 mEq/L |
| calcium ion | 0 to 6 mEq/L |
| chloride ion | 80 to 144 mEq/L |
| (3) albumin | 0.1 to 30 g/L. |

10. A peritoneal dialysis fluid comprising the following composition which has a physiological acceptable pH of 4.0 to 8.0 and an osmotic pressure ratio of dialysis fluid to physiological saline of 1.1 to 3.0,

| (1) glucose | 5 to 45 g/L |
|---|---|
| (2) electrolyte | |
| sodium ion | 120 to 140 mEq/L |
| calcium ion | 2.0 to 5.0 mEq/L |
| magnesium ion | 0.3 to 3.0 mEq/L |
| chloride ion | 80 to 120 mEq/L |
| lactate ion | 10 to 50 mEq/L |
| bicarbonate ion | 0 to 25 mEq/L |
| (3) albumin | 0.1 to 30 g/L. |

11. The peritoneal dialysis fluid as claimed in claim 1, wherein the amount of osmotic agent other than albumin is 5 to 200 g/L.

* * * * *